United States Patent [19]

Hense

[11] 4,299,784
[45] Nov. 10, 1981

[54] APPARATUS FOR PRODUCING AN AEROSOL

[76] Inventor: Günter Hense, Siegfriedstrasse 96, D-4930 Detmold, Fed. Rep. of Germany

[21] Appl. No.: 136,418

[22] Filed: Apr. 2, 1980

[30] Foreign Application Priority Data

Oct. 6, 1978 [DE] Fed. Rep. of Germany ....... 2843756

[51] Int. Cl.³ .............................................. B05B 15/00
[52] U.S. Cl. .................................... 261/78 A; 55/279; 416/3
[58] Field of Search ............... 252/359 R, 359 A, 305; 55/471, 473, 481, 356, 357, 279; 416/3; 415/10, 121 G; 261/DIG. 65, 78 A

[56] References Cited

U.S. PATENT DOCUMENTS

| | | | |
|---|---|---|---|
| 3,116,913 | 1/1964 | Lane | 416/3 X |
| 3,923,482 | 12/1975 | Knab et al. | 55/473 X |
| 3,935,803 | 2/1976 | Bush | 55/473 X |
| 4,043,776 | 8/1977 | Orel | 55/471 X |
| 4,045,192 | 8/1977 | Eckstein et al. | 55/473 X |
| 4,110,419 | 8/1978 | Miller | 261/DIG. 65 X |

*Primary Examiner*—William A. Cuchlinski, Jr.

[57] ABSTRACT

There is disclosed apparatus for producing an aerosol having an atomising chamber having an inlet for material to be atomised, means for atomising the said material, outlet means for the aerosol produced and, inlet means for air, air supply means comprising an air inlet, blower means and an air outlet, means connecting the air outlet of the air supply means to the air inlet of the atomising means and a filter for removing bacteria from the air supplied by the air supply means and drive means connected by a magnetic coupling to the blower means.

The blower means is preferably a fan wheel which is arranged to suck air through the filter, the fan wheel being arranged in a separate chamber which is in the form of a replaceable cassette which can be inserted into the housing of the apparatus, the magnetic coupling acting through a closed wall of the cassette.

12 Claims, 2 Drawing Figures

APPARATUS FOR PRODUCING AN AEROSOL

BACKGROUND OF THE INVENTION

1. Field of the Invention

The present invention relates to apparatus for producing an aerosol having a fan wheel located in a housing and driven by a motor whereby the fan wheel sucks air through a filter to remove bacteria and supplies this purified air to an atomising chamber which atomizes the fluid which it is desired to convert to an aerosol and thus supplies the aerosol.

An aerosol is a gas, especially air, which contains solid or fluid suspended substances in very fine dispersion. Aerosols of water and aqueous solutions with droplet sizes of 1 to 5 μm (microns) are frequently used in medicine, where water-soluble medicaments can be added to the aqueous solutions to produce the aerosol. The aerosols of water and aqueous solutions which are used in medicine serve amongst other things to raise the humidity of the air in operating theatres and intensive care units and to humidify the patients' respiratory tract. It is important here for the aerosols to be germ-free in order to avoid possible infection. Germ-free aerosols can, however, only be produced with apparatus which itself operates in a germ-free manner.

2. Description of the Prior Art

A known apparatus for producing an aerosol for medical purposes (German Offenlegungsschrift No. 2218709) has an atomising chamber to which a fluid is supplied and atomised by means of an oscillator. A blower driven by a motor sucks air in through a filter to remove bacteria and supplies this air to the atomising chamber via a connecting pipe. The air supplied to the atomising chamber mixes with the atomised fluid particles and is discharged as an aerosol from the atomising chamber by means of a hose.

The blower consists of a fan wheel which is located in a separate compartment of a housing which accommodates the other parts of the known apparatus. The fan wheel is rigidly connected via a shaft to a motor which is arranged in its own adjacent compartment of the housing. The fan wheel and the motor together with the wall separating the two adjacent chambers form a closed inseparable unit. In this known apparatus the fan wheel can only be removed from the housing together with the motor and the dividing wall.

It has been found that, despite regular cleaning and changing, the filter provided to remove bacteria which is located in the intake opening of the fan cannot prevent pathogenic agents from collecting in the fan wheel and the space surrounding it and passing through the atomising chamber into the aerosol where they represent a source of infection.

Attempts have been made to arrange a further filter to remove bacteria at the outlet end of the hose leading out of the atomising chamber in order to increase the bacteriological purity of the air which is supplied by the atomiser. However, a filter of this type at the outlet end of the hose dispensing the aerosols absorbs a proportion of the fluid droplets and thereby lowers the humidity content of the aerosol. Furthermore, the fluid droplets absorbed in this filter provide a favourable atmosphere for the pathogenic agents, especially if the aerosol is warmed. As a result the filter at the outlet end of the hose for dispensing the aerosol has to be cleaned or changed after relatively short intervals of time.

SUMMARY OF THE INVENTION

An object of the invention is to provide an apparatus for producing an aerosol in which the danger of infection of the atomised air is reduced and a simple means is provided for sterilising the fan chamber and the pipe from the fan to the atomising chamber.

Thus according to the present invention the fan wheel is located in a separate chamber which is in the form of a replaceable cassette which can be inserted into the housing and the fan wheel is connected to the motor via a magnetic coupling which acts through the closed cassette wall.

DESCRIPTION OF THE PREFERRED EMBODIMENTS

Figure 1:
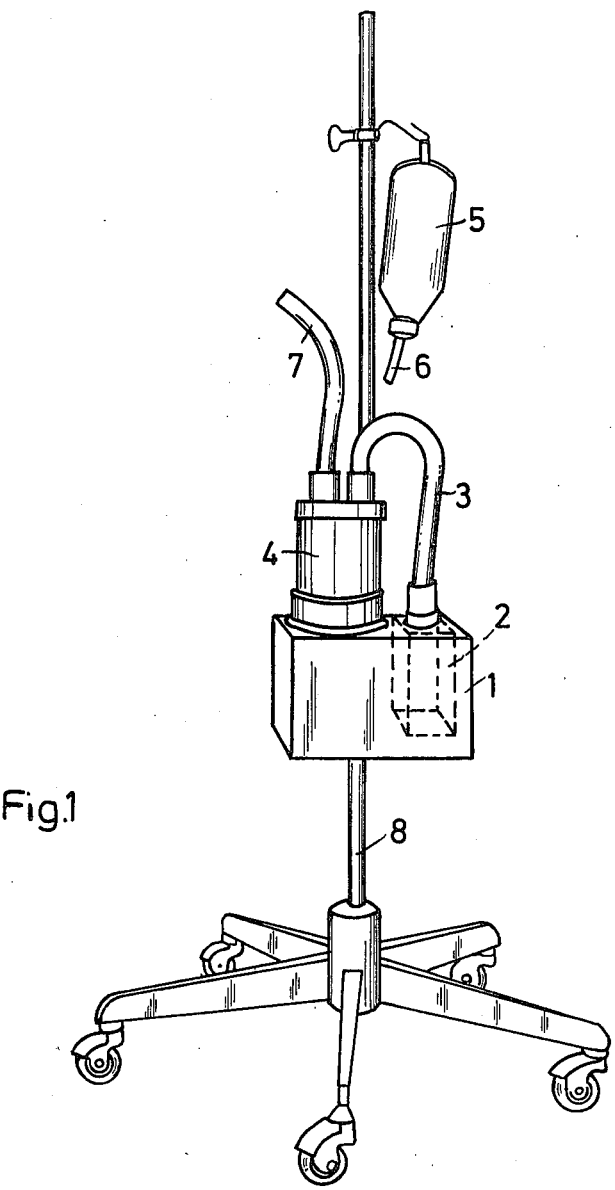

In a preferred form of the invention in an apparatus for producing an aerosol with an atomising chamber to atomise the fluid and supply the aerosol and a fan wheel which is driven by a motor and located in a housing and which sucks air through a bacteria filter and supplies the air to the atomising chamber, the fan wheel is arranged in a separate chamber which is in the form of a replaceable cassette which can be inserted into the housing and the fan wheel is connected to the motor via a magnetic coupling which acts through the closed cassette wall.

The cassette containing the fan wheel and the fan chamber of the apparatus according to the invention thus can be separated easily from the rest of the apparatus and sterilised for example in an autoclave with damp heat at approximately 134° C. or in a steriliser with dry heat at approximately 180° C. No damage can be caused to the motor or other parts of the apparatus by the sterilisation process. The sterilised cassette can then be re-inserted into the guide frame and locked in place. This cassette arrangement according to the invention makes it possible for the unit supplying the quantity of air necessary for production of the aerosol to be cleaned and sterilised regularly without difficulty. If a number of cassettes are available for each apparatus, the apparatus can be used continuously without significant interruption due to cleaning of the cassette since a cassette needing cleaning can be rapidly replaced by a sterile cassette and production of sterile aerosols continued.

The magnetic coupling between the fan wheel and the motor makes it possible to drive the fan wheel without the use of rigid shafts, so that there is no need for any mechanical connection between the drive motor and the fan wheel located in the cassette and the cassette can be inserted and removed without the need to disconnect it from the drive means. The magnetic coupling drives the fan wheel at a speed which is slightly slower than that of the drive motor because of the slippage. The fan wheel may be rotated for example at a speed of the order of 3600 U/min (revs/minutes).

If the cassette is lockable in the housing e.g. by means of leaf springs mounted on a guide frame so that the springs press with their free ends against the outer wall of the cassette, the cassette can on the one hand be effectively retained in position and on the other hand easily removed from the guide frame.

It is possible to achieve perceptible locking of the cassette in the end position by bending the free ends of the leaf springs slightly upwards (or inwardly relative to the aperture in the housing) and providing the external walls of the cassette with small recesses, which the leaf springs can thus engage when the cassette is inserted into the housing. This arrangement has the additional advantage that the cassette can only be released from its locked position by use of a predetermined force, i.e. accidental displacement is made less likely.

If the cassette is supported in the inserted position by an air cushion this results in particularly smooth operation of the fan wheel mounted in the cassette.

The edge or seating of the bacteria removing filter arranged on the cassette can be sealed by providing the cassette with an inwardly-turned shoulder which runs around the air intake and on which the bacteria removing filter is supported. Sealing the seat for the bacteria removing filter prevents air and and with it sources of infection from bypassing the filter and reaching the interior of the cassette.

Simple construction and at the same time efficient operation of the magnetic coupling can be achieved by providing a magnetic disc which is arranged outside the cassette and is driven by the motor and a magnetic disc which is arranged inside the housing of the cassette and is fixed on the shaft of the fan wheel adjacent to the wall of the cassette facing the motor.

Good operation of the magnetic coupling can be achieved by making the magnetic discs from a hub-like disc made from aluminium or copper and a steel ring disc pressed onto the hub-like disc.

The cassette preferably has a handle, since this makes insertion into and removal from the guide frame in the housing considerably easier.

The fan wheel is preferably a radial fan, since this results in an air flow which follows a path which permits the cassette to be small and compact.

The motor is preferably a shaded-pole motor.

The invention also extends to a method of operating apparatus for producing an aerosol in accordance with the invention in which before commencement of production of the aerosol a cassette sterilised in an autoclave at 134° C. in a humid atmosphere and at 180° C. in a dry atmosphere is inserted into the housing and after an operating period of 4 to 8 hours is replaced by a cassette sterilised in an autoclave in the same manner. This cassette may be the same cassette used in the previous operating period or a different one.

DESCRIPTION OF THE BEST MODE OF THE INVENTION

Figure 2:
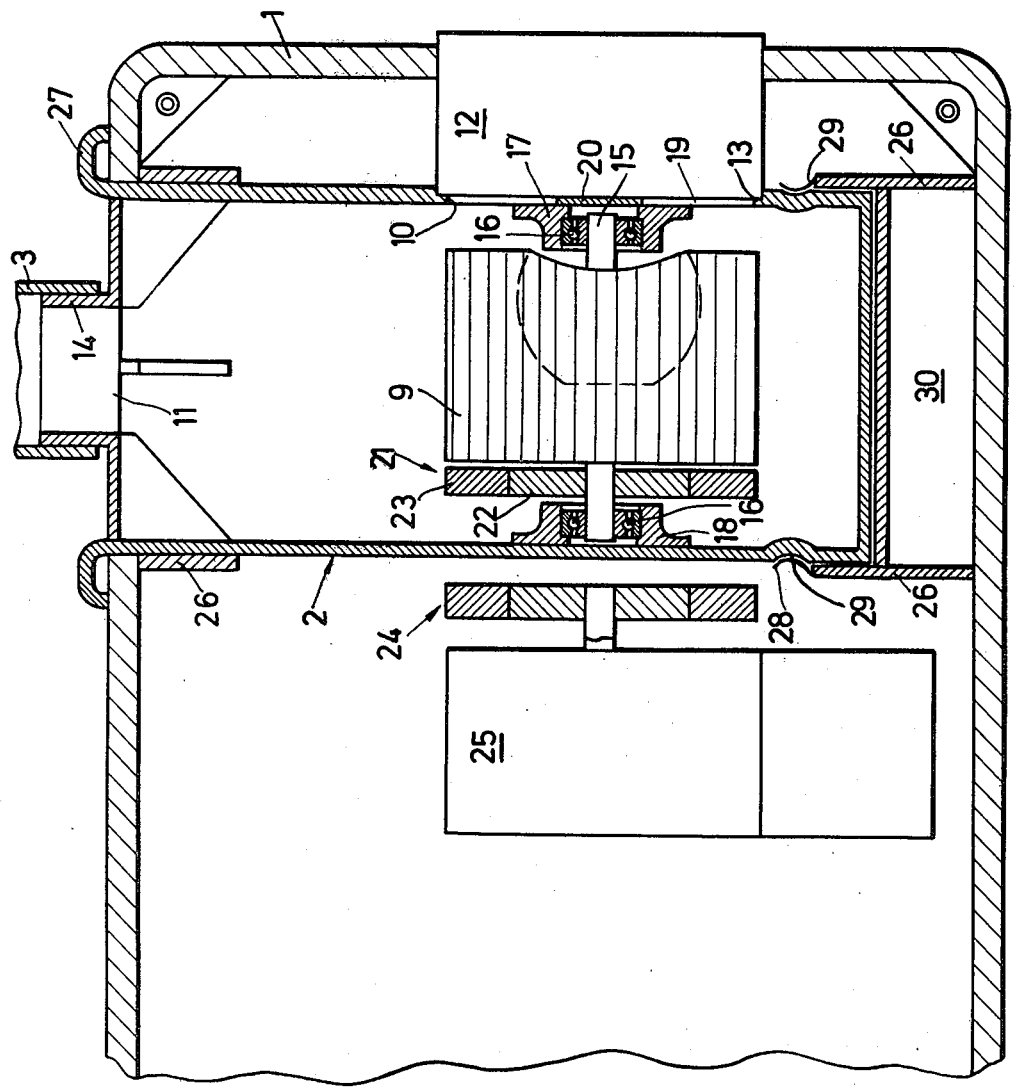

The invention may be put into practice in various ways and one specific embodiment will be described to illustrate the invention with reference to the accompanying drawings, in which:

FIG. 1 is a perspective overall view of an apparatus in accordance with the invention for producing an aerosol; and FIG. 2 is a partial cross-section through the housing shown in FIG. 1 showing the cassette fan wheel arrangement in accordance with the invention.

Referring to FIG. 1, the apparatus for producing an aerosol has a housing 1 in which a cassette 2 (shown in more detail in FIG. 2) is arranged and which supplies the quantity of air necessary for producing the aerosol. The cassette 2 is connected by means of a connecting hose 3 to an atomising chamber 4 with which an oscillator (not shown) is associated. The oscillator atomises a fluid contained in the atomising chamber 4, the fluid being supplied to the atomising chamber 4 from a stock bottle 5 via a hose 6. In FIG. 1 the hose 6 is shown truncated in order not to impair the clarity of the drawing. The fluid to be atomised can be water or an aqueous solution with water-soluble medicaments. The water-soluble medicaments can be added to the fluid in the stock bottle 5 or in the atomising chamber 4. The atomising chamber 4 is provided with an outlet hose 7 from which the aerosol, i.e. the air charged with finely dispersed droplets, emerges and is discharged into the surrounding air or supplied to the respiratory tract of a patient. The apparatus is mounted on a roller stand 8 so that the apparatus can be brought easily and comfortably to the required location.

FIG. 2 shows a cross-section through the housing 1 with the cassette 2 in the location in which it is used to supply the quantity of air necessary for producing the aerosol to the atomising chamber 4 via the connecting hose 3. A fan wheel 9 is arranged inside the cassette 2 and this sucks air in through an intake 10 and discharges it again through an outlet 11. A filter 12 for removing bacteria extends through a side wall of the housing 1 and is arranged in front of the intake 10. The entire circumference of the intake opening 10 is provided with a shoulder 13 on which the bacteria filter 12 is seated in order to provide a sealed connection between the bacteria filter and the cassette and to prevent air bypassing the filter and obtaining access to the interior of the cassette without being filtered. The outlet opening 11 is provided with a connection 14 for the connecting hose 3.

The fan wheel 9 is a radial fan which sucks the air in axially and discharges it radially. The fan wheel 9 is rigidly connected to a shaft 15 arranged inside the cassette. The shaft 15 is rotatably mounted at both ends in ball bearings 16 which are supported in bearing blocks 17 and 18. The bearing block 17 facing the inlet opening 10 is supported on spokes 19 and a central disc 20 carried by the spokes 19. The spokes 19 extend radially over the inlet opening 10. The bearing block 18 is arranged on the inside of the wall of the cassette which is opposite to the wall of the cassette in which the inlet opening 10 is located.

A magnetic disc 21 is rigidly connected to the shaft 15 adjacent the face of the fan wheel 9 facing away from the inlet opening 10. The magnetic disc 21 is located near to the cassette wall and has a hub-like disc 22 made from aluminium or copper and a steel ring disc 23 pressed onto this disc. The magnetic disc 21 is rigidly seated on the shaft 15 for example by pressing the hub-like disc 22 onto the shaft 15.

A further magnetic disc 24 is mounted on the drive shaft of a shaded-pole motor 25.

The disc 24 has the same construction and the same dimensions as the magnetic disc 21 and is aligned axially with the magnetic disc 21. The magnetic disc 24 is located in the immediately proximity of the wall of the cassette towards which the magnetic disc 21 faces but outside the cassette 2.

The two magnetic discs 21 and 24 form a magnetic coupling which drivingly connects the shaded-pole motor 25 to the fan wheel 9. When the shaded-pole motor 25 rotates the fan wheel 9 is driven at the speed of the motor less a certain slippage.

The cassette 2 constitutes a closed unit and is arranged to be pushed into a guide frame 26 on the housing 1. In this way the cassette 2 can be removed from the housing 1 and inserted again, and handles 27 are provided to facilitate manipulation of the cassette 2. Leaf springs 28 are provided which are at least partially bent inwardly of housing 1. As can be seen from FIG. 2 the bent portion of each leaf spring 28 engages in a small recess 29 on the exterior of the cassette 2. Each leaf spring 28 is at one end thereof secured on guide frame 26. When the cassette 2 is inserted as far as its end position the leaf springs 28 engage smoothly and barely audibly in the recess 29 and lock the cassette 2 in its inserted end position. When the cassette 2 is pulled with a certain force on its handles 27 the cassette is released again.

An air cushion 30 is provided within and at the base of the guide frame 26, its object being on the one hand to hold the cassette 2 under a light tension in the locked end position and on the other hand it is intended to absorb operating noise and vibration.

When it is wished to clean the cassette 2 and the filter 12, they can be removed from the housing 1. The filter 12 is first withdrawn laterally from the housing 1, thus releasing the tight fit of the filter 12 in the annular shoulder 13 of the cassette 2. Then the cassette 2 is pulled upwards by the handles 27 out of the housing 1, after first removing the connecting hose 3 from the connection 14. The filter 12 and the cassette 2 with its fan wheel 9 are then sterilised in an autoclave or steriliser. After cleaning, the cassette 2 and the bacteria filter 12 are inserted again into the housing 1 in the same simple manner.

The materials for the construction of the without restriction of their specified function.

Because of the fact that all the elements of the machine which come into contact with the air supplied to the atomising chamber can be sterilised by virtue of the particular construction of the apparatus according to the invention, production of a germ-free aerosol and elimination of sources of infection are facilitated.

What I claim as my Invention and desire to secure by Letters Patent is:

1. In an apparatus for producing an aerosol and which has an atomizing chamber for receiving material to be atomized and a flowing stream of air and delivering an aerosol produced, the apparatus further having air supply means for delivering a flowing stream of air to the atomizing chamber and including fan wheel means for impelling the flowing stream of air, drive means for driving the fan wheel means, and filter means for removing bacteria from air flowing through the fan wheel means, an improvement which facilitates sterilization of the apparatus and comprising replaceable cassette means for containing said fan wheel means and for defining an air flow passageway, housing means for receiving said cassette means and for containing said drive means, and magnetic coupling means operable through a closed wall of said cassette means for coupling said drive means to said fan wheel means, whereby said cassette means may be readily removed from said housing means for sterilization of said cassette means.

2. Apparatus as claimed in claim 1, in which the cassette means containing the fan wheel means is arranged to be insertable and lockable in a guide frame of the housing means.

3. Apparatus as claimed in claim 1, in which the cassette means is engaged by a cushion in the inserted position.

4. Apparatus as claimed in claim 1, in which the magnetic coupling means comprises a magnetic disc which is arranged outside the cassette means and driven by the drive means and a magnetic disc which is arranged inside the cassette means, fixed on a shaft of the fan wheel means near to the wall of the cassette means which faces the drive means.

5. Apparatus as claimed in claim 1, in which the fan wheel means is a radial fan.

6. Apparatus as claimed in claim 1, in which said drive means is a shaded-pole motor.

7. In an apparatus for producing an aerosol and which has an atomizing chamber for receiving material to be atomized and a flowing stream of air and delivering an aerosol produced, the apparatus further having air supply means for delivering a flowing stream of air to the atomizing chamber and including fan wheel means for impelling the flowing stream of air, drive means for driving the fan wheel means, and filter means for removing bacteria from air flowing to the fan wheel means, an improvement which facilitates sterilization of the apparatus and comprising replaceable cassette means for containing said fan wheel means and for defining an air flow passageway, housing means having a guide frame for receiving said cassette means and leaf springs for engaging said cassette means and securing said cassette means in fully inserted position in said guide frame, said housing means further containing said drive means, and magnetic coupling means operable through a closed wall of said cassette means for coupling said drive means and said fan wheel means, whereby said cassette means may be readily removed from said housing means for sterilization of said cassette means.

8. Apparatus as claimed in claim 7, in which the free ends of the leaf springs are bent slightly inwardly of the housing and the cassette walls have small recesses on their exteriors which the leaf springs engage in the inserted end position of the cassette.

9. In an apparatus for producing an aerosol and which has an atomizing chamber for receiving material to be atomized and a flowing stream of air and delivering an aerosol produced, the apparatus further having air supply means for delivering a flowing stream of air to the atomizing chamber and including fan wheel means for impelling the flowing stream of air, drive means for driving the fan wheel means, and filter means for removing bacteria from air flowing to the fan wheel means, an improvement which facilitates sterilization of the apparatus and comprising replaceable cassette means for containing said fan wheel means and for defining an air flow passageway, housing means for receiving said cassette means and for containing said drive means, and magnetic coupling means operable through a closed wall of said cassette means coupling said drive means to said fan wheel means, and further wherein said cassette means has an upwardly turned shoulder portion for sealingly supporting said filter means, whereby said cassette means may be readily removed from said housing means for sterilization of said cassette means.

10. In an apparatus for producing an aerosol and which has an atomizing chamber for receiving material to be atomized and a flowing stream of air and delivering an aerosol produced, the apparatus further having air supply means for delivering a flowing stream of air to the atomizing chamber and including fan wheel means for impelling the flowing stream of air, drive means for driving the fan wheel means, and filter means for removing bacteria from air flowing into the fan wheel means, an improvement which facilitates sterilization of the apparatus and comprising replaceable cassette means for containing said fan wheel means and for defining an air flow passageway, housing means for receiving said cassette means and for containing said drive means, and magnetic coupling means operable through a closed wall of said cassette means for coupling said drive means to said fan wheel means, said magnetic coupling means comprising a magnetic disk mounted within said housing means and driven by said drive means and a magnetic disk mounted within said cassette means and fixed on said fan wheel means, each of said magnetic disks having a hub portion made from nonmagnetic material and an outer disk portion encircling said hub portion and made of ferromagnetic material, whereby said cassette means may be readily removed from said housing means for sterilization of said cassette means.

11. In an apparatus for producing an aerosol and which has an atomizing chamber for receiving material to be atomized and a flowing stream of air and delivering an aerosol produced, the apparatus further having air supply means for delivering a flowing stream of air to the atomizing chamber and including fan wheel means for impelling the flowing stream of air, drive means for driving the fan wheel means, and filter means for removing bacteria from air flowing to the fan wheel means, an improvement which facilitates sterilization of the apparatus and comprising replaceable cassette means for containing said fan wheel means and for defining a air flow passageway, said cassette means having handle means for facilitating manipulation thereof, housing means for receiving said cassette means and for containing said drive means, and magnetic coupling means operable through a closed wall of said cassette means for coupling said drive means to said fan wheel means, said magnetic coupling means comprising a magnetic disk mounted within said housing means and driven by said drive means and a magnetic disk mounted within said cassette and fixed to said fan wheel means, whereby said cassette means may be readily removed from said housing means for sterilization of said cassette means.

12. A method of operating an apparatus for producing an aerosol and which has an atomizing chamber for receiving material to be atomized and a flowing stream of air and delivering an aerosol produced, a cassette containing a fan wheel for delivering the flowing stream of air through the atomizing chamber, a housing for receiving the cassette and for containing a drive for driving the fan, and a magnetic coupling operable through a closed wall of the cassette for coupling the drive to the fan wheel, the method comprising the steps of inserting into the housing before commencement of production of an aerosol a cassette sterilized in an autoclave at 134° C. in a humid atmosphere or at 180° C. in a dry atmosphere and, after an operating period of four to eight hours, replacing the cassette by another cassette sterilized in the same way.

* * * * *